United States Patent [19]

Swezey et al.

[11] Patent Number: 5,158,089
[45] Date of Patent: Oct. 27, 1992

[54] POSTURE-MONITORING HEADBAND DEVICE

[76] Inventors: Robert L. Swezey, 10532 Garwood Rd., Westwood, Calif. 90024; Richard Swezey, 148 N. Wilton Pl., Los Angeles, Calif. 90004

[21] Appl. No.: 726,256
[22] Filed: Jul. 5, 1991
[51] Int. Cl.⁵ .............................. A61B 5/103
[52] U.S. Cl. .................. 128/782; 340/573; 482/909
[58] Field of Search ............ 128/781, 782, 774; 33/512, 366, 370, 371, 372, 373; 273/183 B, DIG. 17; 340/573; 482/909

[56] References Cited

U.S. PATENT DOCUMENTS

| | | | |
|---|---|---|---|
| 2,565,381 | 8/1951 | Leighton | 128/782 |
| 3,582,935 | 6/1971 | Verhaeghe | 340/279 |
| 3,608,541 | 9/1971 | Hall | 128/781 |
| 4,007,733 | 2/1977 | Celeste et al. | 128/781 |
| 4,055,168 | 10/1977 | Miller et al. | 128/781 |
| 4,869,509 | 9/1989 | Lee | 273/183 B |
| 4,871,998 | 10/1989 | Chaillou | 340/573 |
| 4,914,423 | 4/1990 | Fernandez | 340/573 |
| 4,928,709 | 5/1990 | Allison et al. | 128/782 |
| 4,938,476 | 7/1990 | Brunell et al. | 272/93 |
| 5,038,137 | 8/1991 | Lloyd | 340/573 |

*Primary Examiner*—Max Hindenburg
*Assistant Examiner*—Guy V. Tucker
*Attorney, Agent, or Firm*—J. E. McTaggart

[57] ABSTRACT

A monitoring device for posture improvement training, worn as a headband, provides audible feedback of sensed forward or backward deviation from ideal head inclination in the saggital plane. The monitor unit is captivated on an adjustable central strap running front-to-rear over the curvature of the crown of the head. The unit may be moved along the strap to enable initial leveling adjustment to level the unit while the subject's head is maintained in the ideal posture of neutral inclination. A level-sensor, specially mounted in the unit, remains switched in an OFF state as long as the subject's head inclination remains correct, however, whenever the head inclines in either direction in the saggital plane beyond a predetermined critical angle, e.g. 4 degrees, the sensor makes contact to an ON state, actuating a sound-emitting transducer powered by an on-board battery, to indicate the departure from correct posture. Then as soon as the head inclination is corrected within the set limits, the sound is discontinued. To filter out responses to sudden transient head movements, a time delay is introduced between the sensor and the sound transducer; a push switch on mounted on the unit permits the length of the time delay to be set to a BEGINNING value, e.g. 0.5 seconds, or an ADVANCED value, e.g. 0.25 seconds. Other features may include a sun visor, a "sight line" for visual leveling and facilities to accept optional weight inserts for adjusting the sensory effect.

15 Claims, 3 Drawing Sheets

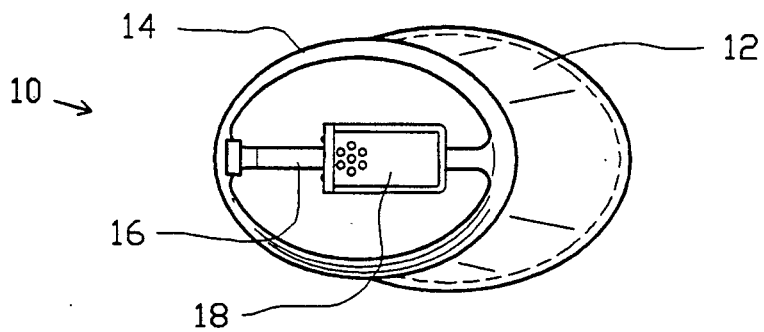
FIG. 1
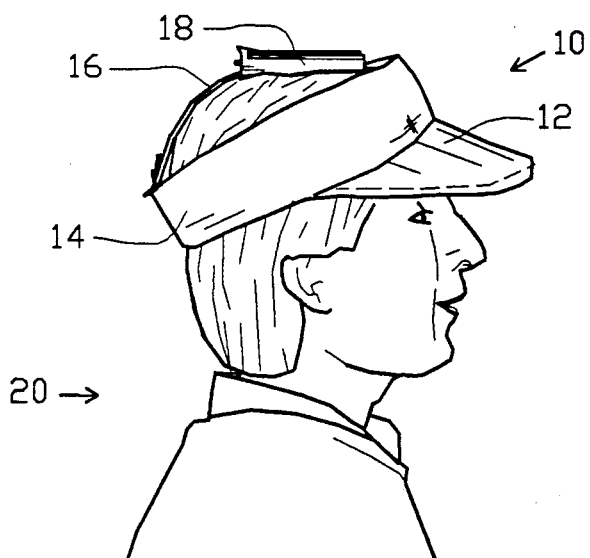
FIG. 2
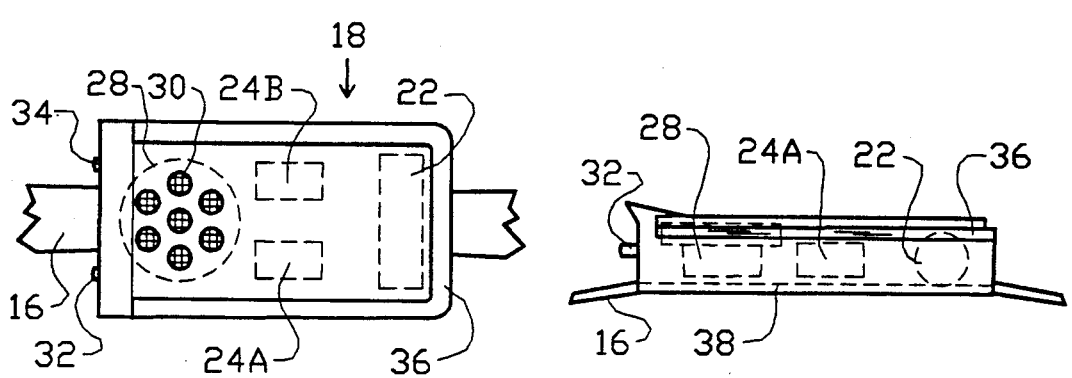
FIG. 3
FIG. 4

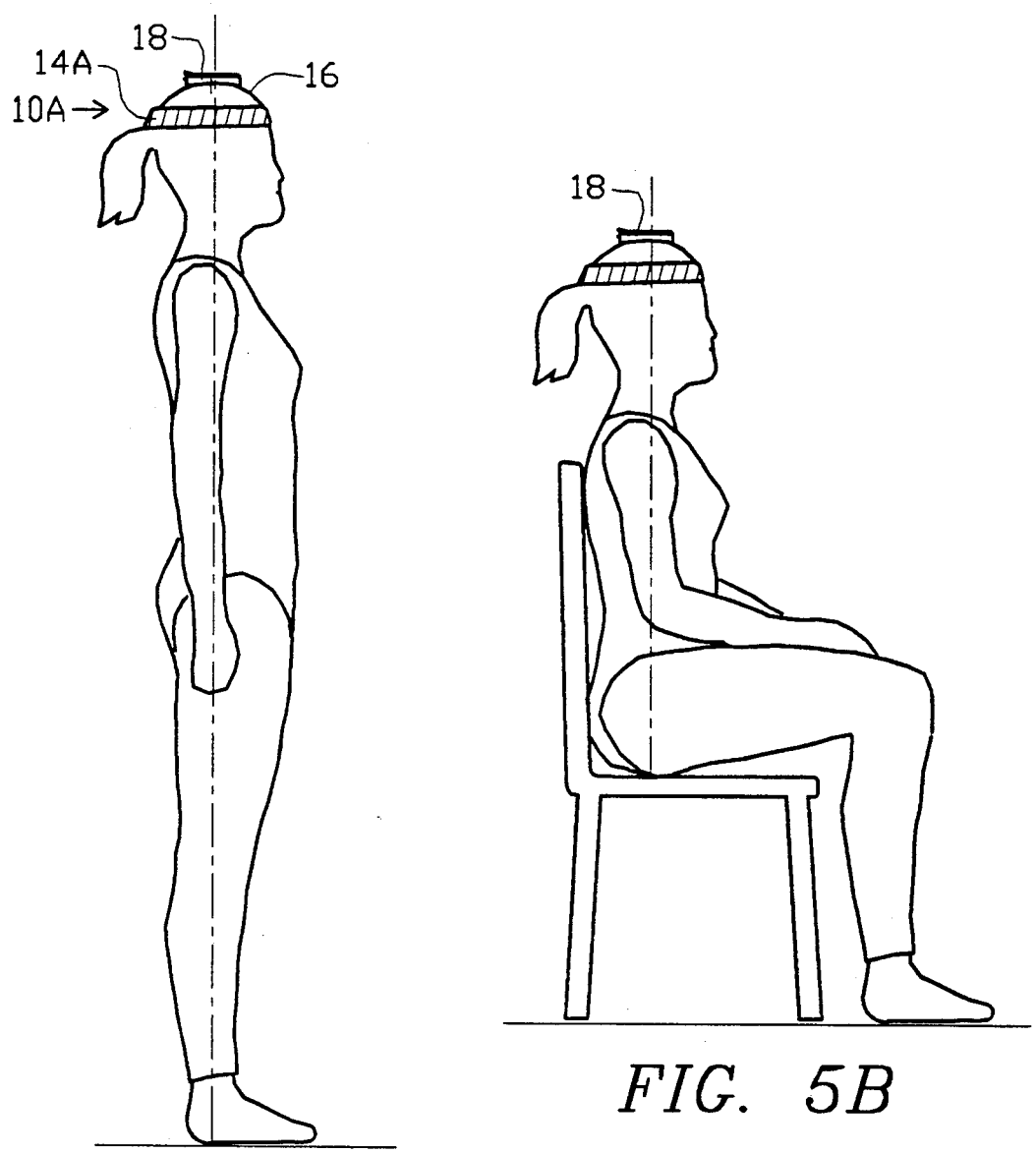
FIG. 5A
FIG. 5B
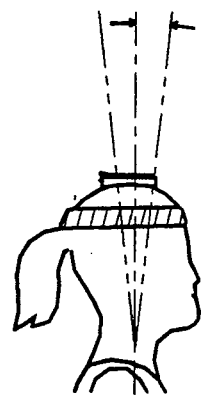
FIG. 5C

POSTURE-MONITORING HEADBAND DEVICE

FIELD OF THE INVENTION

The present invention relates to fitness-training medical apparatus and more particularly it relates to a headband device fitted with means for feeding back positional information to the wearer for purposes of monitoring and improving posture especially as related to the head, neck, shoulders and spine in a standing or sitting position.

BACKGROUND OF THE INVENTION

It has been established that, given symmetry of the body about the saggital plane (the median vertical plane dividing the body into right and left halves), a key element of posture is the inclination of the head in this plane, along with the necessary linear elongation of the neck and spine required for truly good posture. There is an optimal range of head inclination within which the weight of the head tends to be balanced and thus minimize the amount of force required from the supporting muscles. Generally, individuals whose normal head positioning is held within this optimal range tend to enjoy physical wellbeing and good appearance. Outside of this optimal range, unbalancing of the weight of the head upsets the muscle equilibrium, and, if continued over a length of time, generally leads to symptoms of stress and discomfort with risk of progressive deterioration and deformity with aging, along with the resultant disadvantages to the appearance and self-esteem.

For those who seek to overcome harmful posture behavior patterns, a posture training program will benefit from biofeedback and assertive technical reinforcement to accelerate the process and ensure more lasting improvement. Conventional practice often relies heavily on the verbal admonishments of others including professionals and may require an extraordinary level of self-discipline and selfawareness, more than is reasonable to expect in many individuals.

Research leading to the present invention found therapeutic benefit in utilizing a bio-feedback headband device to monitor head inclination in the saggital plane and assertively remind the individual whenever the head position lapses to an incorrect condition. Furthermore, the effectiveness of such treatment may be enhanced by optimizing the amount and distribution of weight in the headband device. The effect of the corrective action extends beyond the actual treatment period by creating within an individual a "muscle-kinesthetic memory" so that even when the device is not in use or activated, the individual actually "recalls" and retains proper head position to the benefit of related neck and back posture.

PRIOR ART

Posture training devices for attachment to the body have been proposed as exemplified by U.S. Pat. No. 4,958,145 to Morris, 4,055,168 to Miller et al, 4,007,733 to Celeste et al, 3,582,935 to Verhaeghe, 3,608,541 to Hall and 4,871,998 to Chailloua; all of these utilize some form of harness or belt for attaching sensing apparatus to the trunk of the body around the waist or shoulders.

U.S. Pat. No. 4,493,328 to Saito discloses a light sensing structure attached to the chest and shoulders operating in conjunction with a head-mounted light source for treating spasmodic torticollis. U.S. Pat. No. 4,869,509 to Lee discloses a GOLFER'S HEAD MOVEMENT INDICATOR as a golfer's training aid which, mounted inside a golfer's cap, audibly signals an improper head motion during a golf swing. The Lee patent further references a number of other patents addressing golfing posture.

The abovementioned and other known art of posture monitoring devices have failed to specifically and satisfactorily apply bio-feedback principles and techniques to therapeutic treatment for correction of the normal standing and sitting posture of individuals afflicted with posture problems.

OBJECTS OF THE INVENTION

It is a primary object of the present invention to provide a headband type device adapted to sense and monitor critical posture data relating to the inclination of the head of an individual wearing the device.

It is a further object to provide an individual wearing the device with biofeedback in accordance with critical posture data as monitored, so as to enable the perception and maintenance of proper posture.

More particularly, it is an object that the device monitor the user's head inclination in the saggital plane and provide audible indication of head inclination beyond certain predetermined critical angles of deviation, both to the front and to the rear.

A still further object is to provide an individual wearing the device with a controllable degree of kinesthetic biofeedback determined by the weight and totter of the device, in addition to audible feedback, to maximize proper spinal elongation.

SUMMARY OF THE INVENTION

The abovementioned objects have been realized in the present invention in an embodiment having a level-sensing head inclination monitoring unit mounted to a headband, which may include a visor, via a central strap positioned along the saggital plane. The unit may be positioned along the strap in an arcuate path over the crown of the head so as to allow the unit to be leveled in the saggital plane. The unit includes a battery powered audible source actuated by a level sensor in response to deviations from a level position. To filter out unwanted response to sudden transient head movements, a selectable time delay may be introduced between the sensor and the sound transducer. Other features may include a "sight line" for visual leveling and facilities to accept optional weight inserts for kinesthetic biofeedback.

BRIEF DESCRIPTION OF THE DRAWINGS

The above and further objects, features and advantages of the present invention will be more fully understood from the following description taken with the accompanying drawings in which:

FIG. 1 is a top view of a posture-monitoring device in accordance with the present invention, having an inclination monitor unit on an adjustable central stap of a visor-equipped headband.

FIG. 2 is a profile of a person wearing the posture-monitoring device of FIG. 1.

FIG. 3 is a top view of the monitor unit of FIG. 1 and FIG. 2.

FIG. 4 is a side view of the monitor unit of FIG. 3.

FIG. 5A is a profile of a second person wearing a headband posture-monitoring device according to present invention, illustrating correct standing posture.

FIG. 5B is a profile of the subject of FIG. 5A illustrating correct sitting posture.

FIG. 5C is a profile of the head of the person of FIGS. 5A and 5B indicating critical angles of head inclination.

DETAILED DESCRIPTION

Figure 6:
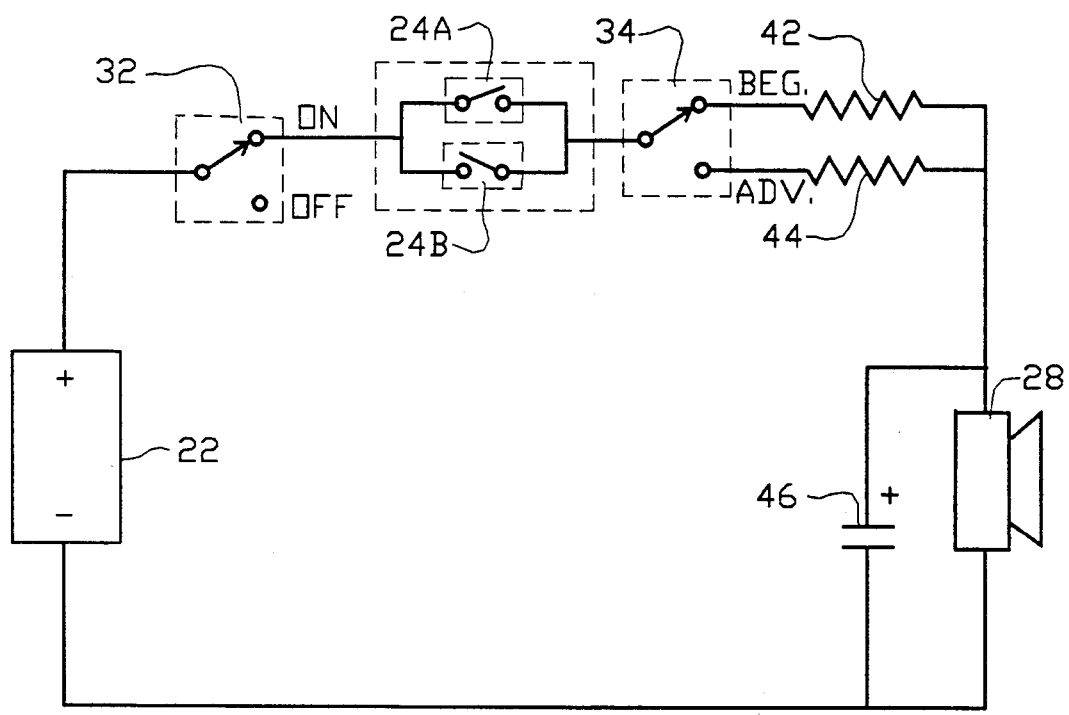
FIG. 6 is a schematic diagram of the monitor unit of FIGS. 1-5C.

In the top view of FIG. 1, a posture-monitoring device 10 of the present invention has a sun visor 12 attached to a headband 14 which has attached to it at a front and rear position a central strap 16 carrying a housing 18 containing a monitor unit which includes an inclination sensor and an audible source. Both the headband 14 and strap 16 are made adjustable for head size by conventional adjusting means such as dome or slide type fastenings.

FIG. 2 is a profile of a person 20 wearing the headgear unit 10 of FIG. 1, showing in side view the visor 12, headband 14, central strap 16 and housing 18. It will be noted that the headband 14 may be worn at an angle, as shown, for comfort, while the housing 18 is in a horizontal position, located toward the front of strap 16. The location of housing 18 along strap 16 is made adjustable thus permitting the housing 18 (and the inclination sensor) to be leveled in the saggital plane of the body by sliding the housing 18 back and forth along strap 16 over the curvature of the top of the head.

FIG. 3 is a top view of the housing 18, indicating the following internal monitor unit components in dashed outline: a 1.5 volt battery 22, a pair of level-sensing switches 24A and 24B constituting the inclination sensor, and a sound transducer 28, located immediately below a set of sound apertures 30. On the rear of housing 18 are located a pair of push switches: ON-OFF switch 32 and BEGINNING-ADVANCED switch 34. A removable U-shaped weight 36 is carried in a peripheral recess on the upper portion of the housing of unit 18.

FIG. 4 is a side view of the unit 18, indicating the following internal monitor unit components in dashed outline: battery 22, level-sensing switch 24A, and sound transducer 28. The ON-OFF push switch 32 appears at the rear, and weight 36 is indicated just below the top surface. It is to be noted that space is provided for addition of a second weight similar to weight 36. The center strap 16 passes through a channel 38 formed in the bottom region of the housing 18.

Switch 24A is positioned in the housing 18 so as to remain off (open circuit) whenever the housing 18 remains horizontal or upwardly inclined at front, but to make contact whenever the housing inclines downwardly at front to a predetermined first critical angle from horizontal. Similarly switch 24B is positioned so as to remain off whenever the housing remains horizontal or downwardly inclined at front but to make contact whenever the housing inclines upwardly at front to a predetermined second critical angle. Typically, in preferred practice as determined for this invention, the first and second critical angle are each set to 4 degrees.

Leveling adjustment requires visual comparison of some form of level sighting line on housing 18 with an external reference level line such as a horizontal room feature or actual outdoor horizon. The sighting line may be provided as a distinguishable marking on each side of housing 18.

FIG. 5A is a profile of a person wearing a posture-monitoring unit 10A of this invention, illustrating correct posture in a standing position: the vertical line indicates generally linear alignment of the spine, neck and head in balanced relationship. In this instance the headband 14A is made without a visor and is worn in an approximately horizontal position to accommodate the person's hair styling. As in FIG. 2, housing 18 is leveled in the body's saggital plane by sliding the housing 18 back and forth along strap 16 over the curvature of the top of the head.

In FIG. 5B the same subject is profiled in a sitting position, again illustrating correct posture with linear spine, neck and head alignment, with housing 18 leveled.

FIG. 5C, shows a profile of the head of the subject of FIGS. 5A and 5B. Critical angles of head inclination are indicated by phantom lines each side of the vertical line as the head is inclined back and forth in the saggital axis about a pivot point located in the neck region. Head inclination within the critical angles is considered indicative of acceptably normal posture, while inclination beyond the critical angles indicate defective posture and need for corrective action. Studies indicate the critical angles fall within a range between 2 and 7 degrees; for purposes of this invention a value of 4 degrees in both the plus and minus directions is suggested.

In FIG. 6, the schematic diagram of the monitor unit, a battery 22 is connected through the ON-OFF (pushbutton) switch 32, shown in its ON position, to the two level-sensing switches 24A and 24B, connected in parallel. The BEGINNING-ADVANCED switch 34 is wired to energize transducer 28 through a first resistor 42 in its BEGINNING position and through a second resistor 44 in its ADVANCED position. A capacitor 46 is connected in parallel with transducer 28, and serves to introduce a time delay in the initiation of sound following closing of either switch 24A or 24B. The length of the delay is determined by an RC time constant set by the resistance values of resistors 42 and 44 so that two values of time delay may be set independently: one for the BEGINNING position and one for the ADVANCED position.

In the operation of the device 10, the headband 14 is adjusted to the user's head size and center band 16 is adjusted to hold housing 18 in a comfortable and secure substantially horizontal position. Then with the head held at a correct inclination, the housing 18 is adjusted back and forth until it is precisely horizontal as described above in connection with sighting line 40 in FIG. 4. At this point when power switch 32 is turned on there is no sound from the transducer 28 because both level-sensing switches 24A and 24B are level, thus open. Assuming switch 34 is set to the BEGINNING position, if the head is allowed to incline forward beyond the critical angle, then switch 24A closes; then, after the time delay required for capacitor 46 to charge up though resistor 42, transducer 28 will become energized and emit sound to indicate that the head position has inclined beyond the set limit. Similarly head inclination to the rear beyond the critical angle will result in switch 24B closing and transducer 28 emitting sound after the delay of charging capacitor 46 through resistor 42. Setting switch 34 to the ADVANCED position removes resistor 42 from the circuit replacing it with resistor 44 which has a lower resistance, providing a shorter time delay. Typical time delay values which are recommended as optimal are: 0.5 seconds for BEGINNING and 0.25 seconds for ADVANCED.

The weight 36, FIGS. 3 and 4, may be stamped from suitable metal such as lead or steel. The function of the weight 36 is to provide kinesthetic biofeedback continuously whenever the device is worn, via sensory head region contact of the headband 14 and central strap 16, independent of the acoustic feedback of the monitor unit. Weight 36 allows for the optimal elongation of the neck and spine by a slight sensation of weight on top of the head. The optimal weight value is determined empirically, typically ranging between 1 and 6 ounces. Generally the weight is selected near the high end of this range at the beginning of posture training and may be reduced as training progresses.

Flexibility in training options is provided by the ability to utilize a variable degree of kinesthetic biofeedback as selected by the variable weight, with or without the audible feedback system in operation.

In a particular embodiment of the device as shown in FIG. 1 the headband is made from neoprene with a fabric covering. The housing 18 is injection molded.

There are a number of options available in the implementation of the device to accommodate particular requirements and training philosophies.

Switches 24A and 24B may be readily implemented as mercury switches; alternatively they may be implemented in some other functionally equivalent form capable of level-sensing contact closure.

Switches 32 and 34 could be implemented in other form such as slide, rocker or rotary switches, and/or could be combined in a single switch unit.

The indication delay time for the forward inclination could be made to be different from that for rearward inclination through the provision of an additional pole in switch 34 and two additional timing resistors, in a simple circuit change.

A sighting may not be required if the housing 18 is made to have a profile in which the top edge is flat, readily visible and suited to serve directly as a sighting edge. Alternatively, if the profile of housing 18 is too low for convenient direct sighting then the sighting line could be implemented by a special flip-up mechanism.

The invention may be embodied and practiced in other specific forms without departing from the spirit and essential characteristics thereof. The present embodiments are therefore to be considered in all respects as illustrative and not restrictive, the scope of the invention being indicated by the appended claims rather than by the foregoing description; and all variations, substitutions and changes which come within the meaning and range of equivalency of the claims are therefore intended to be embraced therein.

What is claimed is:

1. A posture-monitoring headband device comprising:
    a headband, adjustable in circumference, adapted to be worn by a human subject;
    a strap, attached to said headband at a front location and at a rear location, traversing overtop the subject's head in an arcuate path located substantially in a saggital body plane;
    a housing, having on a bottom side thereof strap attachment means captively engaging said strap in a manner disposing said housing substantially above said strap with freedom to be adjustably positioned along said arcuate path over a range including an operational position in which a predetermined normal disposition of subject's head results in a substantially level horizontal position of the housing;
    level-sensing means, disposed within said housing, adapted to sense predetermined deviations from said level horizontal position in the subject's saggital plane; and
    indicating means adapted to indicate said deviations kinesthetically to the subject.

2. The posture-monitoring device as defined in claim 1 wherein said level-sensing means comprises:
    a first level-sensing switch disposed in particular orientation relative to said housing so as to change contact state whenever said housing deviates from said level position, in a first direction in the saggital plane, beyond a first predetermined angle, and
    a second level-sensing switch disposed in particular orientation relative to said housing so as to change contact state whenever the position of said housing deviates from said level position, in a second direction in the saggital plane, opposite the first direction, beyond a second predetermined angle.

3. The posture-monitoring device as defined in claim 2 wherein the first and second predetermined angles are each designated to be within a range between 2 degrees and 7 degrees.

4. The posture-monitoring device as defined in claim 3 wherein said first level-sensing switch and said second level-sensing switch are implemented as single-pole-single-throw mercury-type switches connected in parallel with each other, and are mounted in an orientation such as to present an open circuit when said housing is located in said level position.

5. The posture-monitoring device as defined in claim 4 said indicating means comprises an audible sound transducer connected in an electrical circuit along with said two parallel-connected mercury-type switches, a battery and an on-off switch, said circuit being adapted to cause said transducer to emit an audible sound in response to either of said switches making contact.

6. The posture-monitoring device as defined in claim 5 further comprising time delay means in said circuit adapted to introduce a time delay of predetermined duration between the time of either of said switches making contact and the initiation of audible sound emitted from said transducer.

7. The posture-monitoring device as defined in claim 6 wherein said time delay means comprises a capacitor connected in parallel with said transducer and a resistor connected in series in a circuit path between said battery and said capacitor.

8. The posture-monitoring device as defined in claim 6 further comprising time delay selection means, associated in said circuit with said time delay means, adapted to enable the subject to set said time delay to a selected one of at least two predetermined values of time delay duration.

9. The posture-monitoring device as defined in claim 8 wherein said time delay means comprises:
    a capacitor connected in parallel with said transducer;
    a first resistor, sized in resistance to provide, in conjunction with said capacitor, a first predetermined time delay;
    a second resistor, sized in resistance to provide, in conjunction with said capacitor, a second predetermined time delay; and
    a selector switch adapted to enable selection of either one of said first or said second resistor, thusly selecting said first or said second predetermined time delay.

10. The posture-monitoring device as defined in claim 9 wherein:
   the first time delay is made to be approximately 0.5 seconds and a corresponding position of said selector switch is designated BEGINNING, and
   the second time delay is made to be approximately 0.25 seconds and a corresponding position of said selector switch is designated ADVANCED.

11. The posture-monitoring device as defined in claim 1 further comprising a first metallic weighting part removably attached to said housing in a recessed upper peripheral region thereof.

12. The posture-monitoring device as defined in claim 11 further comprising a second metallic weighting part removably attached to said housing in the recessed upper peripheral region thereof.

13. A posture-monitoring headband device comprising:
   a headband, adjustable in circumference, adapted to be worn by a human subject;
   a strap, attached to said headband at a front location and at a rear location, traversing overtop the subject's head in an arcuate path located substantially in a saggital body plane;
   a housing, having on a bottom side thereof strap attachment means captively engaging said strap in a manner such as to dispose said housing substantially above said strap with freedom to be adjustably positioned along said arcuate path over a range including an operational position in which a predetermined normal disposition of subject's head results in a substantially level horizontal position of said housing;
   level sensing means, disposed within said housing, comprising a pair of parallel-connected switches adapted to change from an open state to a closed state whenever subject's head becomes inclined beyond a designated angle of deviation in either direction in the saggital plane from said normal disposition;
   indicating means, including a battery, cooperating with said level sensing means so as to provide an audible indication in response to said switches changing to a closed state; and
   delay means, in an electrical circuit including said level sensing means and said indicating means, adapted to introduce a predetermined time delay between the time of said switches changing to a closed state and the time of initiation of a consequential audible indication.

14. The posture-monitoring headband device as defined in claim 13 further comprising switch and associated circuit means adapted to enable switchable selection of said predetermined time delay from a choice of at least two predetermined values.

15. The posture-monitoring headband device as defined in claim 13 further comprising a supplemental weighting accessory part, having a designated weight, removably attached to an upper peripheral region of said housing.

* * * * *